(12) United States Patent
Sjoeholm et al.

(10) Patent No.: US 7,658,965 B2
(45) Date of Patent: *Feb. 9, 2010

(54) USE OF ACID STABLE PROTEASE IN ANIMAL FEED

(75) Inventors: Carsten Sjoeholm, Alleroed (DK); Peter Rahbek Oestergaard, Virum (DK)

(73) Assignee: DSM Assets B.V., Heerlen (NL)

(*) Notice: Subject to any disclaimer, the term of this patent is extended or adjusted under 35 U.S.C. 154(b) by 643 days.

This patent is subject to a terminal disclaimer.

(21) Appl. No.: 10/713,394

(22) Filed: Nov. 14, 2003

(65) Prior Publication Data

US 2004/0161448 A1    Aug. 19, 2004

Related U.S. Application Data

(63) Continuation of application No. 09/779,323, filed on Feb. 8, 2001, now Pat. No. 6,855,548.

(60) Provisional application No. 60/183,133, filed on Feb. 17, 2000.

(30) Foreign Application Priority Data

Feb. 8, 2000    (DK) ............................ 2000 00200

(51) Int. Cl.
 *A23J 1/00* (2006.01)
(52) U.S. Cl. .................................... 426/656
(58) Field of Classification Search ............... 435/422, 435/220; 426/656, 7, 4
See application file for complete search history.

(56) References Cited

U.S. PATENT DOCUMENTS

| | | |
|---|---|---|
| 3,652,399 A | 3/1972 | Isono et al. |
| 3,674,643 A | 7/1972 | Aunstrup et al. |
| 3,683,069 A | 8/1972 | Hooreman et al. |
| 3,723,250 A | 3/1973 | Aunstrup et al. |
| 3,823,072 A | 7/1974 | Hooreman et al. |
| 3,868,448 A | 2/1975 | Hahn et al. |
| 3,966,971 A | 6/1976 | Morehouse et al. |
| 4,052,262 A | 10/1977 | Horikoshi et al. |
| 4,062,732 A | 12/1977 | Lehmann et al. |
| 4,073,884 A | 2/1978 | Hartdegan et al. |
| 4,218,437 A | 8/1980 | Hiller |
| 4,225,584 A | 9/1980 | Hiller |
| 4,239,750 A | 12/1980 | Hiller |
| 4,429,044 A | 1/1984 | Boguslawski et al. |
| 4,473,644 A | 9/1984 | Schindler et al. |
| 4,480,037 A | 10/1984 | Ichishima et al. |
| 4,518,697 A | 5/1985 | Bartnik et al. |
| 5,047,240 A | 9/1991 | Hooreman et al. |
| 5,312,748 A | 5/1994 | Liu et al. |
| 5,597,720 A | 1/1997 | Outtrup et al. |
| 5,646,028 A | 7/1997 | Leigh |
| 5,705,379 A | 1/1998 | Wilson et al. |
| 5,811,382 A | 9/1998 | Damhus et al. |
| 6,558,693 B1 | 5/2003 | Knap et al. |
| 6,855,548 B2 * | 2/2005 | Sjoeholm et al. ............. 435/422 |
| 7,179,630 B2 * | 2/2007 | Lassen et al. ................ 435/212 |
| 2006/0143738 A1 | 6/2006 | Lassen |
| 2006/0147499 A1 * | 7/2006 | Oestergaard et al. ........ 424/442 |
| 2006/0236414 A1 | 10/2006 | Lassen |
| 2007/0104764 A1 | 5/2007 | Jensen et al. |

FOREIGN PATENT DOCUMENTS

| | | |
|---|---|---|
| DE | 200432 | 9/1981 |
| DE | 2004328 | 9/1981 |
| EP | 130756 | 1/1985 |
| EP | 0 300 466 | 1/1989 |
| EP | 0 506 448 | 9/1992 |
| EP | 0 647 710 | 4/1995 |
| EP | 897985 | 2/1999 |
| EP | 908105 | 4/1999 |
| JP | 02255081 | 10/1990 |
| JP | 2003/284571 | 10/2003 |
| WO | WO 88/03947 | 6/1988 |
| WO | WO 91/10723 | 7/1991 |
| WO | WO 93/24623 | 12/1993 |
| WO | WO 95/02044 | 1/1995 |
| WO | WO 95/21540 | 8/1995 |
| WO | WO 95/28850 | 11/1995 |
| WO | WO 96/05739 | 2/1996 |
| WO | WO 98/56260 | 12/1998 |
| WO | WO 99/53038 | 10/1999 |
| WO | WO 01/58275 | 8/2001 |
| WO | WO 01/58276 | 8/2001 |
| WO | WO 2004/070106 | 8/2004 |
| WO | WO 2004/072221 | 8/2004 |
| WO | WO 2004/072279 | 8/2004 |
| WO | WO 2004/111219 | 12/2004 |
| WO | WO 2004/111220 | 12/2004 |
| WO | WO 2004/111221 | 12/2004 |
| WO | WO 2004/111222 | 12/2004 |
| WO | WO 2004/111223 | 12/2004 |

OTHER PUBLICATIONS

Refsite et al., Aquaculture, vol. 162, pp. 301-302, (1998).
Needleman et al., J Mol Biol, vol. 48, pp. 443-453, (1970).
Michalik et al., UKR Biokhre, vol. 69, Part 3, pp. 28-35 (1997).
Gillet al., Analytical Biochemistry, vol. 182, pp. 319-326, (1989).
Kaneda et al., J. Biochem, vol. 78, pp. 1287-1296, (1975).

(Continued)

*Primary Examiner*—Maryam Monshipouri
(74) *Attorney, Agent, or Firm*—Elias Lambris (57) ABSTRACT

The present invention relates to acid-stable proteases homologous to those derived from strains of the genus Nocardiopsis, their use in animal feed, feed-additives and feed compositions containing such proteases, and methods for the treatment of vegetable proteins using such proteases.

8 Claims, 2 Drawing Sheets

OTHER PUBLICATIONS

Caine et al., Animal Feed Science and Technology, vol. 71, pp. 177-183, (1998).
Atschul et al., SEQ ID No. 2, Serine Proteinase, GenPept (1997).
MEROPS Database, Alignment of Subfamily S1E peptidases (2004).
Sidhut et al., The Journal of Biological Chemistry, vol. 269 No. 31, pp. 20167-20171 (1994).
Henderson et al., Journal of Bacteriology, vol. 169, No. 8, pp. 3778-3784 (1987).
Mitsuiki et al., Bioscience Biotechnol Biochemistry, vol. 66, No. 1, pp. 164-167 (2002).
Gayle et al., The Journal of Biological Chemistry, vol. 268, No. 29, pp. 22105-22111 (1993).
Whistock et al., Quarterly Reviews of Biophysics, vol. 36, No. 3, pp. 307-340 (2003).
Sequence Alignment of Protein disclosed in PCT/DK96/00013, Accession AAW92997 (1999).
Sequence Alignment of protein disclosed in WO 2001/58276, Accession No. AAU07125 (2003).
Sequence Alignment of protein disclosed in PCT/DK96/00013, Accession No. AAX22316 (1999).
Tsuijibo et al., Journal of Applied Bacteriology, vol. 69, No. 4, pp. 520-529 (1990).
Tsuijibo et al., Agric Biol. Chem. vol. 54, No. 8, pp. 2177-2179 (1990).
Sequence Alignment with protease disclosed in EP 506448, Derwent GeneSeq Nucleotide, accession No. AAQ29011 (2004).
Tsuijibo et al., Applied and Environmental Microbiology, vol. 69, No. 2, pp. 894-900 (2003).
O Fagain, Enzyme and Microbiol Technology, vol. 33, pp. 137-149 (2003).
Database EMBL, Accession No. AY151208, "Nocardiopsis sp. TOA-1 serine protease (napA) gene, complete cds," XP-002308395 (May 16, 2004).
Mitsuiki et al., Enzyme and Microbiol Technology, vol. 34, pp. 482-489 (2004).
Kim et al., Korean Biochemical Journal, vol. 26, No. 1, pp. 81-85 (1993).
Moreira et al., World Journal of Microbiology & Biotechnology, vol. 18, pp. 307-312 (2002).
Screen et al., Journal of Biological Chemistry, vol. 275, No. 9, pp. 6689-6694 (2000).
Lao et al., Applied and Environmental Microbiology, vol. 62, No. 11, pp. 4256-4259 (1996).
Dixit et al., Biochimica, vol. 1523, pp. 261-268 (2000).
Van Heynigen, European Journal of Biochemistry, vol. 28, pp. 432-437 (1972).
Van Heynigen, Biochem. Journal, vol. 125, pp. 1159-1160 (1971).
Barrett et al., Handbook of Proteolytic Enzymes, pp. 887-890 (1998).
Higgins et al, Gene, vol. 73, pp. 237-244 (1989).
Smith, Analytical Biochemistry, vol. 150, pp. 76-85 (1985).
Antibiotic Enzymes, Abstract of SU 779383 (1980).

* cited by examiner

SEQUENCE LISTING

```
<160> NUMBER OF SEQ ID NOS: 2

<210> SEQ ID NO 1
<211> LENGTH: 188
<212> TYPE: PRT
<213> ORGANISM: Nocardiopsis sp. NRRL 18262

<400> SEQUENCE: 1
```

```
Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65              70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
                100                 105                 110

Thr Ile Gln Ala Arg Gly Gln Ser Val Ser Tyr Pro Glu Gly Thr Val
            115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
                180                 185

<210> SEQ ID NO 2
<211> LENGTH: 17
<212> TYPE: PRT
<213> ORGANISM: Nocardiopsis alba

<400> SEQUENCE: 2

Ala Asp Ile Ile Gly Gly Leu Ala Tyr Thr Met Gly Gly Arg Cys Ser
1               5                   10                  15

Val
```

USE OF ACID STABLE PROTEASE IN ANIMAL FEED

CROSS-REFERENCE TO RELATED APPLICATIONS

This application is a continuation of application Ser. No. 09/779,323 filed Feb. 8, 2001, now U.S. Pat. No. 6,855,548, which claims priority or the benefit under 35 U.S.C. 119 of Danish application no. PA 2000 00200 filed Feb. 8, 2000 and U.S. provisional application no. 60/183,133 filed Feb. 17, 2000, the contents of which are fully incorporated herein by reference.

BACKGROUND OF THE INVENTION

1. Field of the Invention

The present invention relates to the use of acid-stable proteases in animal feed (in vivo), and to the use of such proteases for treating vegetable proteins (in vitro).

Proteins are essential nutritional factors for animals and humans. Most livestock and many human beings get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal solids is not digested. For example, the apparent ileal protein digestibility in piglets and growing pigs is only around 80%.

The stomach of mono-gastric animals and many fish exhibits a strongly acidic pH. Most of the protein digestion, however, occurs in the small intestine. A need therefore exists for an acid-stable protease that can survive passage of the stomach.

2. State of the Art

The use of proteases in animal feed, or to treat vegetable proteins, is known from the following documents:

WO 95/28850 discloses i.a. an animal feed additive comprising a phytase and a proteolytic enzyme. Various proteolytic enzymes are specified at p. 7.

WO 96/05739 discloses an enzyme feed additive comprising xylanase and a protease. Suitable proteases are listed at p. 25.

WO 95/02044 discloses i.a. proteases derived from *Aspergillus aculeatus*, as well as the use in animal feed thereof.

U.S. Pat. No. 3,966,971 discloses a process of obtaining protein from a vegetable protein source by treatment with an acid phytase and optionally a proteolytic enzyme. Suitable proteases are specified in column 2.

U.S. Pat. Nos. 4,073,884, 5,047,240, 3,868,448, and 3,823,072, and 3,683,069 describe protease preparations derived from various strains of *Streptomyces* and their use in animal feed.

These proteases, however, are not acid-stable and/or are not homologous to the proteases described herein.

SUMMARY OF THE INVENTION

Proteases have now been identified which are found to be very acid-stable, and expectedly of an improved performance in animal feed.

BRIEF DESCRIPTION OF DRAWINGS

The present invention is further illustrated by reference to the accompanying drawings, in which.

DETAILED DESCRIPTION OF THE INVENTION

The term protease as used herein is an enzyme that hydrolyzes peptide bonds (has protease activity). Proteases are also called e.g. peptidases, proteinases, peptide hydrolases, or proteolytic enzymes.

Preferred proteases for use according to the invention are of the endo-type that act internally in polypeptide chains (endopeptidases). Endopeptidases show activity on N- and C-terminally blocked peptide substrates that are relevant for the specificity of the protease in question.

Included in the above definition of protease are any enzymes belonging to the EC 3.4 enzyme group (including each of the thirteen sub-subclasses thereof) of the EC list (Enzyme Nomenclature 1992 from NC-IUBMB, 1992),as regularly supplemented and updated, see e.g. the World Wide Web (WWW) at www.chem.qmw.ac.uk/iubmb/enzyme/index.html.

Proteases are classified on the basis of their catalytic mechanism into the following groupings: serine proteases (S), cysteine proteases (C), aspartic proteases (A), metalloproteases (M), and unknown, or as yet unclassified, proteases (U), see Handbook of Proteolytic Enzymes, A. J. Barrett, N. D. Rawlings, J. F. Woessner (eds), Academic Press (1998), in particular the general introduction part.

The *Nocardiopsis* proteases disclosed herein are serine proteases.

In a particular embodiment the proteases for use according to the invention are serine proteases. The term serine protease refers to serine peptidases and their clans as defined in the above Handbook. In the 1998 version of this handbook, serine peptidases and their clans are dealt with in chapters 1-175. Serine proteases may be defined as peptidases in which the catalytic mechanism depends upon the hydroxyl group of a serine residue acting as the nucleophile that attacks the peptide bond. Examples of serine proteases for use according to the invention are proteases of Clan SA, e.g. Family S2 (Streptogrisin), e.g. Sub-family S2A (alpha-lytic protease), as defined in the above Handbook.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 5, 6, 7, 8, 9, 10, or 11. Examples of assay-temperatures are 25, 30, 35, 37, 40, 45, 50, 55, 60, 65, or 70° C.

Examples of protease substrates are casein, and pNA-substrates, such as Suc-AAPF-pNA (available e.g. from Sigma S-7388). The capital letters in this pNA-substrate refers to the one-letter amino acid code. Another example is Protazyme AK (azurine-dyed crosslinked casein prepared as tablets by Megazyme T-PRAK). For pH-activity and pH-stability studies, the pNA-substrate is preferred, whereas for temperature-activity studies, the Protazyme AK substrate is preferred.

Examples of protease assays are described in the experimental part.

There are no limitations on the origin of the protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e.g. by Site-directed Mutagenesis, by PCR (using a PCR fragment containing the desired mutation as one of the primers in the PCR reactions), or by Random Mutagenesis. The preparation of consensus proteins is described in e.g. EP 897985.

Examples of acid-stable proteases for use according to the invention are (i) the proteases derived from *Nocardiopsis* sp. NRRL 18262, and *Nocardiopsis alba*;

(ii) proteases of at least 60, 65, 70, 75, 80, 85, 90, or at least 95% amino acid identity to any of the proteases of (i);

(iii) proteases of at least 60, 65, 70, 75, 80, 85, 90, or at least 95% identity to any of SEQ ID NO: 1, and/or SEQ ID NO: 2.

For calculating percentage identity, any computer program known in the art can be used. Examples of such computer programs are the Clustal V algorithm (Higgins, D. G., and Sharp, P. M. (1989), Gene (Amsterdam), 73, 237-244; and the GAP program provided in the GCG version 8 program package (Program Manual for the Wisconsin Package, Version 8, Genetics Computer Group, 575 Science Drive, Madison, Wis., USA 53711) (Needleman, S. B. and Wunsch, C. D., (1970), Journal of Molecular Biology, 48, 443-453.

When using the Clustal V algorithm for calculating the percentage of identity between two protein sequences, a PAM250 residue weight table is used, together with the default settings of the MegAlign program, v4.03, in the Lasergene software package (DNASTAR Inc., 1228 South Park Street, Madison, Wis. 53715, US). Default settings for multiple alignments are a gap penalty of 10 and a gap length penalty of 10. For calculating percentage identity between two protein sequences the following settings are used: Ktuple of 1, gap penalty of 3, window of 5, and 5 diagonals saved.

When using GAP, the following settings are applied for polypeptide sequence comparison: GAP creation penalty of 5.0 and GAP extension penalty of 0.3.

In a particular embodiment, the protease for use according to the invention is a microbial protease, the term microbial indicating that the protease is derived from, or originates from, a microorganism, or is an analogue, a fragment, a variant, a mutant, or a synthetic protease derived from a microorganism. It may be produced or expressed in the original wild-type microbial strain, in another microbial strain, or in a plant; i.e. the term covers the expression of wild-type, naturally occurring proteases, as well as expression in any host of recombinant, genetically engineered or synthetic proteases.

The term microorganism as used herein includes Archaea, bacteria, fungi, vira etc.

Examples of microorganisms are bacteria, e.g. bacteria of the phylum Actinobacteria phy.nov., e.g. of class I: Actinobacteria, e.g. of the Subclass V: Actinobacteridae, e.g. of the Order I: Actinomycetales, e.g. of the Suborder XII: Streptosporangineae, e.g. of the Family II: Nocardiopsaceae, e.g. of the Genus I; *Nocardiopsis*, e.g. *Nocardiopsis* sp. NRRL 18262, and *Nocardiopsis alba*; or mutants or variants thereof exhibiting protease activity. This taxonomy is on the basis of Bergey's Manual of Systematic Bacteriology, $2^{nd}$ edition, 2000, Springer (preprint: Road Map to Bergey's).

Further examples of microorganisms are fungi, such as yeast or filamentous fungi.

In another embodiment the protease is a plant protease. An example of a protease of plant origin is the protease from the sarcocarp of melon fruit (Kaneda et al, J. Biochem. 78, 1287-1296 (1975).

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the protease can be fed to the animal before, after, or simultaneously with the diet. The latter is preferred.

In the present context, the term acid-stable means, that the protease activity of the pure protease enzyme, in a dilution corresponding to $A_{280}=1.0$, and following incubation for 2 hours at 37° C. in the following buffer:

100 mM succinic acid, 100 mM HEPES, 100 mM CHES, 100 mM CABS, 1 mM $CaCl_2$, 150 mM KCl, 0.01% Triton® X-100, pH 3.5, is at least 40% of the reference activity, as measured using the assay described in Example 2C herein (substrate: Suc-MPF-pNA, pH 9.0, 25° C.).

In particular embodiments of the above acid-stability definition, the protease activity is at least 45, 50, 55, 60, 65, 70, 75, 80, 85, 90, 95, or at least 97% of the reference activity.

The term reference activity refers to the protease activity of the same protease, following incubation in pure form, in a dilution corresponding to $A_{280}=1.0$, for 2 hours at 5° C. in the following buffer: 100 mM succinic acid, 100 mM HEPES, 100 mM CHES, 100 mM CABS, 1 mM $CaCl_2$, 150 mM KCl, 0.01% Triton® X-100, pH 9.0, wherein the activity is determined as described above.

In other words, the method of determining acid-stability comprises the following steps:

a) The protease sample to be tested (in pure form, $A_{280}=1.0$) is divided in two aliquots (I and II);

b) Aliquot I is incubated for 2 hours at 37° C. and pH 3.5;

c) Residual activity of aliquot I is measured (pH 9.0 and 25° C.);

d) Aliquot II is incubated for 2 hours at 5° C. and pH 9.0;

e) Residual activity of aliquot II is measured (pH 9.0 and 25° C.);

f) Percentage residual activity of aliquot I relative to residual activity of aliquot II is calculated.

Alternatively, in the above definition of acid-stability, the step b) buffer pH-value may be 1.0, 1.5, 2.0, 2.5, 3.0, 3.1, 3.2, 3.3, or 3.4.

In other alternative embodiments of the above acid-stability definition relating to the above alternative step b) buffer pH-values, the residual protease activity as compared to the reference, is at least 5, 10, 15, 20, 25, 30, 35, 40, 45, 50, 55, 60, 65, 70, 75, 80, 85, 90, 95, or at least 97%.

In alternative embodiments, pH values of 6.0, 6.5, 7.0, 7.5, 8.0, or 8.5 can be applied for the step d) buffer.

In the above acid-stability definition, the term $A_{280}=1.0$ means such concentration (dilution) of said pure protease which gives rise to an absorption of 1.0 at 280 nm in a 1 cm path length cuvette relative to a buffer blank.

And in the above acid-stability definition, the term pure protease refers to a sample with a $A_{280}/A_{260}$ ratio above or equal to 1.70 (see Example 2E), and which by a scan of a Coomassie-stained SDS-PAGE gel is measured to have at least 95% of its scan intensity in the band corresponding to said protease (see Example 2A). In the alternative, the $A_{280}/A_{260}$ ratio is above or equal to 1.50, 1.60, 1.65, 1.70, 1.75, 1.80, 1.85, or above or equal to 1.90.

However, for the uses according to the invention, the protease need not be that pure; it may e.g. include other enzymes, even other proteases, in which case it could be termed a protease preparation. Nevertheless, a well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

In a particular embodiment, the protease, in the form in which it is added to the feed, or when being included in a feed additive, is well-defined. Well-defined means that the protease preparation is at least 50% pure as determined by Size-exclusion chromatography (see Example 8).

In other particular embodiments the protease preparation is at least 60, 70, 80, 85, 88, 90, 92, 94, or at least 95% pure as determined by this method.

In the alternative, the term well-defined means, that a fractionation of the protease preparation on an appropriate Size-exclusion column reveals only one major protease component.

The skilled worker will know how to select an appropriate Size-exclusion chromatography column. He might start by fractionating the preparation on e.g. a HiLoad26/60 Superdex75 pg column from Amersham Pharmacia Biotech (see Example 8). If the peaks would not be clearly separated he would try different columns (e.g. with an amended column particle size and/or column length), and/or he would amend the sample volume. By simple and common trial-and-error methods he would thereby arrive at a column with a sufficient resolution (clear separation of peaks), on the basis of which the purity calculation is performed as described in Example 8.

The protease preparation can be (a) added directly to the feed (or used directly in the treatment process of vegetable proteins), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

In one particular embodiment, the protease for use according to the invention, besides being acid-stable, also has a pH-activity optimum close to neutral.

The term pH-activity optimum close to neutral means one or more of the following: That the pH-optimum is in the interval of pH 6.0-11.0, or pH 7.0-11.0, or pH 6.0-10.0, or pH 7.0-10.0, or pH 8.0-11.0, or pH 8.0-10.0 (see Example 2B and FIG. 2 herein).

In another particular embodiment, the protease for use according to the invention, besides being acid-stable, is also thermostable.

The term thermostable means one or more of the following: That the temperature optimum is at least 50° C., 52° C., 54° C., 56° C., 58° C., 60° C., 62° C., 64° C., 66° C., 68° C., or at least 70° C., reference being made to Example 2D and FIG. 3 herein.

In a further particular embodiment, the protease for use according to the invention is capable of solubilizing vegetable proteins according to the in vitro model of Example 4 herein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The treatment according to the invention of vegetable proteins with at least one acid-stable protease results in an increased solubilization of vegetable proteins.

The following are examples of % solubilized protein obtainable using the proteases of the invention: At least 74.0%, 74.5%, 75.0%, 75.5%, 76.0%, 76.5%, 77.0%, or at least 77.5%, reference being had to the in vitro model of Example 4 herein.

The term solubilization of proteins basically means bringing protein(s) into solution. Such solubilization may be due to protease-mediated release of protein from other components of the usually complex natural compositions such as feed. Solubilization can be measured as an increase in the amount of soluble proteins, by reference to a sample with no protease treatment (see Example 4 herein).

In a particular embodiment of a treatment process the protease(s) in question is affecting (or acting on, or exerting its solubilizing influence on the vegetable proteins or protein sources. To achieve this, the vegetable protein or protein source is typically suspended in a solvent, e.g. an aqueous solvent such as water, and the pH and temperature values are adjusted paying due regard to the characteristics of the enzyme in question. For example, the treatment may take place at a pH-value at which the relative activity of the actual protease is at least 50, or 60, or 70, or 80 or 90%. Likewise, for example, the treatment may take place at a temperature at which the relative activity of the actual protease is at least 50, or 60, or 70, or 80 or 90% (these relative activities being defined as in Example 2 herein). The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the vegetable proteins or protein sources, but its solubilizing influence is so to speak not switched on until later when desired, once suitable solubilizing conditions are established, or once any enzyme inhibitors are inactivated, or whatever other means could have been applied to postpone the action of the enzyme.

In one embodiment the treatment is a pre-treatment of animal feed or vegetable proteins for use in animal feed, i.e. the proteins are solubilized before intake.

The term improving the nutritional value of an animal feed means improving the availability of the proteins, thereby leading to increased protein extraction, higher protein yields, and/or improved protein utilisation. The nutritional value of the feed is therefore increased, and the growth rate and/or weight gain and/or feed conversion (i.e. the weight of ingested feed relative to weight gain) of the animal is/are improved.

The protease can be added to the feed in any form, be it as a relatively pure protease, or in admixture with other components intended for addition to animal feed, i.e. in the form of animal feed additives, such as the so-called pre-mixes for animal feed.

Animal Feed Additives

Apart from the acid-stable protease, the animal feed additives of the invention contain at least one fat-soluble vitamin, and/or at least one water-soluble vitamin, and/or at least one trace mineral, and/or at least one macro mineral.

Further, optional, feed-additive ingredients are coloring agents, aroma compounds, stabilisers, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4 (EC refers to Enzyme Classes according to Enzyme Nomenclature 1992 from NC-IUBMB, 1992), see also the World Wide Web (WWW) at www.chem.qmw.ac.uk/iubmb/enzyme/index.html.

In a particular embodiment these other enzymes are well-defined (as defined and exemplified above for protease preparations, i.a. by reference to Example 8).

Usually fat- and water-soluble vitamins, as well as trace minerals form part of a so-called premix intended for addition to the feed, whereas macro minerals are usually separately added to the feed. Either of these composition types, when enriched with an acid-stable protease according to the invention, is an animal feed additive of the invention.

In a particular embodiment, the animal feed additive of the invention is intended for being included (or prescribed as having to be included) in animal diets or feed at levels of 0.01-10.0%; more particularly 0.05-5.0%; or 0.2-1.0% (% meaning g additive per 100 g feed). This is so in particular for premixes.

Accordingly, the concentrations of the individual components of the animal feed additive, e.g. the premix, can be found by multiplying the final in-feed concentration of the same component by, respectively, 10-10000; 20-2000; or 100-500 (referring to the above three percentage inclusion intervals).

Guidelines for desired final concentrations, i.e. in-feed-concentrations, of such individual feed and feed additive components are indicated in Table A below.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components—exemplified with poultry and piglets/pigs—are listed in Table A below. Nutritional requirement means that these components should be provided in the diet in the concentrations indicated. These data are compiled from:

NRC, Nutrient requirements in swine, ninth revised edition 1988, subcommittee on swine nutrition, committee on animal nutrition, board of agriculture, national research council. National Academy Press, Washington, D.C. 1988; and NRC, Nutrient requirements of poultry, ninth revised edition 1994, subcommittee on poultry nutrition, committee on animal nutrition, board of agriculture, national research council. National Academy Press, Washington, D.C. 1994.

In the alternative, the animal feed additive of the invention comprises at least one of the individual components specified in Table A. At least one means either of, one or more of, one, or two, or three, or four and so forth up to all thirteen, or up to all fifteen individual components.

More specifically, this at least one individual component is included in the additive of the invention in such an amount as to provide an in-feed-concentration within the range indicated in column four, or column five, or column six of Table A.

As explained above, corresponding feed additive concentrations can be found by multiplying the interval limits of these ranges with 10-10000; 20-2000; or 100-500. As an example, considering which premix-content of vitamin A would correspond to the feed-content of 10-10000 IU/kg, this exercise would lead to the following intervals: $100-10^8$ IU; or $200-2\times10^7$ IU; or $1000-5\times10^6$ IU per kg additive.

TABLE A

| Nutrients provided per kg diet | Nutrient requirements - and preferred ranges | | | | |
|---|---|---|---|---|---|
| | Poultry | Piglets/Pigs/Sows | Range 1 | Range 2 | Range 3 |
| Fat-soluble vitamins | | | | | |
| Vitamin A/[IU] | −5000 | 1300-4000 | 10-10000 | 50-8000 | 100-6000 |
| Vitamin D3/[IU] | −1100 | 150-200 | 2-3000 | 5-2000 | 10-1500 |
| Vitamin E/[IU] | −12 | 11-22 | 0.02-100 | 0.2-80 | 0.5-50 |
| Vitamin K/[mg] | 0.5-1.5 | −0.5 | 0.005-10.0 | 0.05-5.0 | 0.1-3.0 |

TABLE A-continued

Nutrient requirements - and preferred ranges

| Nutrients provided per kg diet | Poultry | Piglets/Pigs/ Sows | Range 1 | Range 2 | Range 3 |
|---|---|---|---|---|---|
| Water-soluble vitamins | | | | | |
| $B_{12}$/[mg] | −0.003 | 0.005-0.02 | 0.0001-1.000 | 0.0005-0.500 | 0.001-0.100 |
| Biotin/[mg] | 0.100-0.25 | 0.05-0.08 | 0.001-10.00 | 0.005-5.00 | 0.01-1.00 |
| Choline/[mg] | 800-1600 | 300-600 | 1-10000 | 5-5000 | 10-3000 |
| Trace minerals | | | | | |
| Manganese/[mg] | −60 | 2.0-4.0 | 0.1-1000 | 0.5-500 | 1.0-100 |
| Zinc/[mg] | 40-70 | 50-100 | 1-1000 | 5-500 | 10-300 |
| Iron/[mg] | 50-80 | 40-100 | 1-1000 | 5-500 | 10-300 |
| Copper/[mg] | 6-8 | 3.0-6.0 | 0.1-1000 | 0.5-100 | 1.0-25 |
| Iodine/[mg] | −0.4 | −0.14 | 0.01-100 | 0.05-10 | 0.1-1.0 |
| Selenium/[mg] | −0.2 | 0.10-0.30 | 0.005-100 | 0.01-10.0 | 0.05-1.0 |
| Macro minerals | | | | | |
| Calcium/[g] | 8-40 | 5-9 | 0.1-200 | 0.5-150 | 1-100 |
| Phosphorus, as available phosphorus/[g] | 3-6 | 1.5-6 | 0.1-200 | 0.5-150 | 1-50 |

Animal Feed Compositions

Animal feed compositions or diets have a relatively high content of protein. According to the National Research Council (NRC) publications referred to above, poultry and pig diets can be characterised as indicated in Table B below, columns 2-3. Fish diets can be characterised as indicated in column 4 of Table B. Furthermore such fish diets usually have a crude fat content of 200-310 g/kg. These fish diet are exemplified with diets for Salmonids and designed on the basis of Aquaculture, principles and practices, ed. T. V. R. Pillay, Blackwell Scientific Publications Ltd. 1990; Fish nutrition, second edition, ed. John E. Halver, Academic Press Inc. 1989.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B below (R. 2-5).

Crude protein is calculated as nitrogen (N) multiplied by a factor 6.25, i.e. Crude protein (g/kg)=N (g/kg)×6.25 as stated in Animal Nutrition, 4th edition, Chapter 13 (Eds. P. McDonald, R. A. Edwards and J. F. D. Greenhalgh, Longman Scientific and Technical, 1988, ISBN 0-582-40903-9). The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient Requirements of Swine (1988) pp. 2-6, and the European Table of Energy Values for Poultry Feedstuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix. The final enzyme concentration in the diet is within the range of 0.01-200 mg enzyme protein per kg diet, for example in the range of 5-30 mg enzyme protein per kg animal diet.

Examples of animal feed compositions are shown in Example 7.

TABLE B

Range values for energy, protein and minerals in animal diets

| Nutrient | Poultry Min-Max | Piglets/Pigs/Sows Min-Max | Fish Min-Max | R. 1 | R. 2 | R. 3 | R. 4 | R. 5 |
|---|---|---|---|---|---|---|---|---|
| Metabolizable energy, MJ/kg | 12.1-13.4 | 12.9-13.5 | 14-25 | 10-30 | 11-28 | 11-26 | 12-25 | |
| Crude protein, g/kg | 124-280 | 120-240 | 300-480 | 50-800 | 75-700 | 100-600 | 110-500 | 120-490 |
| Calcium, g/kg | 8-40 | 5-9 | 10-15 | 0.1-200 | 0.5-150 | 1-100 | 4-50 | |
| Available Phosphorus, g/kg | 2.1-6.0 | 1.5-5.5 | 3-12 | 0.1-200 | 0.5-150 | 1-100 | 1-50 | 1-25 |
| Methionine, g/kg | 3.2-5.5 | — | 12-16 | 0.1-100 | 0.5-75 | 1-50 | 1-30 | |
| Methionine plus Cysteine, g/kg | 4-9 | 2.3-6.8 | — | 0.1-150 | 0.5-125 | 1-80 | | |
| Lysine, g/kg | 2.5-11 | 6-14 | 12-22 | 0.5-50 | 0.5-40 | 1-30 | | |

In particular embodiments of the method of the invention for treating vegetable proteins, a further step of adding phytase is also included. And in further particular embodiments, in addition to the combined treatment with phytase and protease, further enzymes may also be added, wherein these enzymes are selected from the group comprising other proteases, phytases, lipolytic enzymes, and glucosidase/carbohydrase enzymes. Examples of such enzymes are indicated in WO 95/28850.

The protease should of course be applied in an effective amount, i.e. in an amount adequate for improving solubilization and/or improving nutritional value of feed. It is at present contemplated that the enzyme is administered in one or more of the following amounts (dosage ranges): 0.01-200; or 0.01-100; or 0.05-100; or 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives.

Of course, if a sample is available of the protease used for preparing the feed additive or the feed, the specific activity is determined from this sample (no need to purify the protease from the feed composition or the additive).

Many vegetables contain anti-nutritional factors such as lectins and trypsin inhibitors. The most important anti-nutritional factors of soybean are the lectin soybean agglutinin (SBA), and the soybean trypsin inhibitor (STI).

Lectins are proteins that bind to specific carbohydrate-containing molecules with considerable specificity, and when ingested they become bound to the intestinal epithelium. This may lead to reduced viability of the epithelial cells and reduced absorption of nutrients.

SBA is a glycosylated, tetrameric lectin with a subunit molecular weight of about 30 kDa and a high affinity for N-acetylgalactosamine.

Trypsin inhibitors affect the intestinal proteolysis reducing protein digestibility, and also increase the secretion of digestive enzymes from the pancreas leading to a loss of amino acids in the form of digestive enzymes. An example of a trypsin inhibitor is the Bowman-Birk Inhibitor, which has a molecular weight of about 8 kDa, contains 7 disulfide bridges and has two inhibitory loops specific for trypsin-like and chymotrypsin-like proteases. Other examples are the so-called Kunitz Inhibitors of Factors (e.g. the Soybean Kunitz Trypsin Inhibitor that contains one binding site for trypsin-like proteases and has a molecular weight of about 20 kDa).

The proteases for use according to the invention have been shown to hydrolyze anti-nutritional factors like SBA lectin, and the trypsin inhibitors Bowman Birk Inhibitor and The Soybean Kunitz Factor. See the experimental part, Example 5.

Thus, the invention also relates to the use of acid-stable proteases for hydrolysing, or reducing the amount of, anti-nutritional factors, e.g. SBA lectin, and trypsin inhibitors, such as the Bowman Birk Inhibitor, and Kunitz Factors, such as the Soybean Kunitz Factor.

EXAMPLE 1

Screening for Acid-Stable Proteases

A large number of proteases were analyzed for stability at pH 3, with the objective of identifying proteases that have the necessary stability to pass through the acidic stomach of mono-gastric animals.

The proteases had been purified by conventional chromatographic methods such as ion-exchange chromatography, hydrophobic interaction chromatography and size exclusion chromatography (see e.g. Protein Purification, Principles, High Resolution Methods, and Applications. Editors: Jan-Christer Janson, Lars Rydén, VCH Publishers, 1989).

Protease activity was determined as follows: The protease was incubated with 1.67% Hammarsten casein at 25° C., pH 9.5 for 30 minutes, then TCA (tri-chloro acetic acid) was added to a final concentration of 2% (w/w), the mixture was filtrated to remove the sediment, and the filtrate was analyzed for free primary amino groups (determined in a colometric assay based on OPA (o-phthal-dialdehyde) by measuring the absorbance at 340 nm, using a serine standard (Biochemische Taschenbuch teil II, Springer-Verlag (1964), p. 93 and p. 102). One Casein Protease Unit (CPU) is defined as the amount of enzyme liberating 1 mmol of TCA-soluble primary amino groups per minute under standard conditions, i.e. 25° C. and pH 9.5.

The proteases were diluted to an activity of 0.6 CPU/l in water, divided in two aliquots and each aliquot was then further diluted to 0.3 CPU/l with 100 mM citrate buffer, pH 3, and 100 mM phosphate buffer, pH 7 respectively. The diluted samples were incubated at 37° C. for 1 hour, and 20 microliters of the samples were applied to holes in 1% agarose plates containing 1% skim milk. The plates (pH 7.0) were incubated at 37° C. over night and clearing zones were measured.

A number of proteases performed well in this test, and the following two have now been characterised: The *Nocardiopsis alba* and *Nocardiopsis* sp. NRRL 18262 proteases described in Example 2. The strain of *Nocardiopsis alba* has been deposited according to the Budapest Treaty on the International Recognition of the Deposit of Microorganisms for the Purposes of Patent Procedure at DSMZ-Deutsche Sammlung von Mikroorganismen und Zellkulturen GmbH, Mascheroder Weg 1b, D-38124 Braunschweig, Germany, as follows:

| Deposit date | 22 Jan. 2001 |
|---|---|
| CBS No. | *Nocardiopsis alba* DSM 14010 |

Purification

The culture broth was centrifuged at 10000×g for 30 minutes in 1 liter beakers. The supernatants were combined and further clarified by a filtration though a Seitz K-250 depth filter plate. The clear filtrate was concentrated by ultrafiltration on a 3 kDa cut-off polyether sulfone cassette (Filtron). The concentrated enzyme was transferred to 50 mM $H_3BO_3$, 5 mM 3,3'-dimethyl glutaric acid, 1 mM $CaCl_2$, pH 7 (Buffer A) on a G25 Sephadex column (Amersham Pharmacia Biotech), and applied to a Bacitracin agarose column (Upfront Chromatography A/S) equilibrated in Buffer A. After washing the Bacitracin column with Buffer A to remove unbound protein, the protease was eluted from the column using Buffer A supplemented with 25% 2-propanol and 1 M sodium chloride. The fractions with protease activity were pooled and transferred to 20 mM $CH_3COOH/NaOH$, 1 mM $CaCl_2$, pH 4.5 (Buffer B) by chromatography on a G25 Sephadex column (Amersham Pharmacia Biotech). The buffer exchanged protease pool was applied to a SOURCE 30S column (Amersham Pharmacia Biotech) equilibrated in Buffer B. After washing the SOURCE 30S column with Buffer B, the protease was eluted with an increasing linear NaCl gradient (0 to 0.25 M) in Buffer B. Fractions from the column were tested for protease activity and protease containing fractions were analyzed by SDS-PAGE. Pure fractions were pooled and used for further characterization.

The protease of *Nocardiopsis* sp. NRRL 18262 was prepared using conventional methods, as generally described above for the protease of *Nocardiopsis*.

Characterization

The protease derived from *Nocardiopsis alba* was found to have a molecular weight of Mr=21 kDa (SDS-PAGE), and the following partial (N-terminal (MVS)) amino acid sequence was determined: ADIIGGLAYTMGGRCSV (SEQ ID NO: 2).

The protease derived from *Nocardiopsis* sp. NRRL 18262 has the following sequence of 188 amino acids:

ADIIGGLAYTMGGRCSVGFAATNAAGQPGFVTAGHCGRVGTQVTIGNGRGVFEQSVFPGNDA    (SEQ ID NO: 1)

AFVRGTSNFTLTNLVSRYNTGGYAAVAGHNQAPIGSSVCRSGSTTGWHCGTIQARGQSVSYP

EGTVTNMTRTTVCAEPGDSGGSYISGTQAQGVTSGGSGNCRTGGTTFYQEVTPMVNSWGV

RLRT.

The deposit was made by Novozymes A/S and was later assigned to Hoffmann-La Roche AG.

EXAMPLE 2

Preparation, Characterization and Comparative Study of *Nocardiopsis* Proteases Fermentation

*Nocardiopsis alba* was inoculated from tryptone yeast agar plates into shake flasks each containing 100 ml HG-23 medium with the following composition: Oatmeal 45 g/l, Yeast Extract 2 g/l, di-sodium hydrogen phosphate 12 g/l, Potassium di-hydrogen phosphate 6 g/l, Pluronic PE 6100 0.2 ml/l in distilled water. The strain was fermented for 9 days at 37 degree C.

The purpose of this characterisation was to study their pH-stability, pH-activity and temperature-activity profiles, in comparison to Sub. Novo, Sub. Novo (Y217L), and SAVINASE™.

Sub. Novo is subtilisin from *Bacillus amyloliquefaciens*, and Sub. Novo (Y217L) is the mutant thereof that is disclosed in WO 96/05739. Sub. Novo was prepared and purified from a culture of the wild-type strain using conventional methods, whereas the mutant was prepared as described in Examples 1-2, and 15-16 of EP 130756.

SAVINASE™ is a subtilisin derived from *Bacillus clausii* (previously *Bacillus lentus* NCIB 10309), commercially available from Novozymes A/S, Krogshoejvej, DK-2880 Bagsvaerd, Denmark. Its preparation is described in U.S. Pat. No. 3,723,250.

EXAMPLE 2A

Determination of SDS-PAGE Purity of Protease Samples

The SDS-PAGE purity of the protease samples was determined by the following procedure:

40 microliters protease solution ($A_{280}$ concentration=0.025) was mixed with 10 microliters 50% (w/v) TCA (trichloroacetic acid) in an Eppendorf tube on ice. After half an hour on ice the tube was centrifuged (5 minutes, 0° C., 14.000×g) and the supernatant was carefully removed. 20 microliters SDS-PAGE sample buffer (200 microliters Tris-Glycine SDS Sample Buffer (2×) (125 mM Tris/HCl, pH 6.8, 4% (w/v) SDS, 50 ppm bromophenol blue, 20% (v/v) Glycerol, LC2676 from NOVE™)+160 microliters dist. water+20 microliters beta-mercaptoethanol+20 microliters 3 M unbuffered Tris Base (Sigma T-1503) was added to the precipitate and the tube was boiled for 3 minutes. The tube was centrifuged shortly and 10 microliter sample was applied to a 4-20% gradient Tris-Glycine precast gel from NOVE™ (polyacrylamide gradient gel based on the Laemmli chemistry but without SDS in the gel, (Laemmli, U.K., (1970) Nature, vol. 227, pp. 680-685), EC60255). The electrophoresis was performed with Tris-Glycine running buffer (2.9 g Tris Base, 14.4 g Glycine, 1.0 g SDS, distilled water to 1 liter) in both buffer reservoirs at a 150V constant voltage until the bromophenol blue tracking dye had reached the bottom of the gel. After electrophoresis, the gel was rinsed 3 times, 5 minutes each, with 100 ml of distilled water by gentle shaking. The gel was then gently shaked with Gelcode® Blue Stain Reagent (colloidal Comassie G-250 product from PIERCE, PIERCE cat. No. 24592) for one hour and washed by gentle shaking for 8 to 16 hours with distilled water with several changes of distilled water. Finally, the gel was dried between 2 pieces of cellophane. Dried gels were scanned with an Arcus II scanner from AGFA equipped with Fotolook 95 v2.08 software and imported to the image evaluation software CREAM™ for Windows (catalogue nos. 990001 and 990005, Kem-En-Tec, Denmark) by the File/Acquire command with the following settings (of Fotolook 95 v2.08): Original=Reflective, Mode=Color RGB, Scan resolution=240 ppi, Output resolution=120lpi, Scale factor=100%, Range=Histogram with Global selection and Min=0 and Max=215, ToneCurve=None, Sharpness=None, Descreen=None and Flavor=None, thereby producing an *.img picture file of the SDS-PAGE gel, which was used for evaluation in CREAM™. The *.img picture file was evaluated with the menu command Analysis/1-D. Two scan lines were placed on the *.img picture file with the Lane Place Tool: A Sample scan line and a Background scan line. The Sample scan line was placed in the middle of a sample lane (with the protease in question) from just below the application slot to just above the position of the Bromphenol blue tracking dye. The Background scan line was placed parallel to the Sample scan line, but at a position in the pictured SDS-PAGE gel where no sample was applied, start and endpoints for the Background scan line were perpendicular to the start and endpoints of the Sample scan line. The Background scan line represents the true background of the gel. The width and shape of the scan lines were not adjusted. The intensity along the scan lines where now recorded with the 1-D/Scan menu command with Medium sensitivity. Using the 1-D/Editor menu command, the Background scan was subtracted from the Sample scan. Then the 1-D/Results menu command was selected and the Area % of the protease peak, as calculated by the CREAM™ software, was used as the SDS-PAGE purity of the proteases.

All the protease samples had an SDS-PAGE purity of above 95%.

EXAMPLE 2B pH-Activity Assay

Suc-AAPF-pNA (Sigma® S-7388) was used for obtaining pH-activity profiles.

Assay buffer: 100 mM succinic acid (Merck 1.00682), 100 mM HEPES (Sigma H-3375), 100 mM CHES (Sigma C-2885), 100 mM CABS (Sigma C-5580), 1 mM $CaCl_2$, 150 mM KCl, 0.01% Triton® X-100, adjusted to pH-values 3.0, 4.0, 5.0, 6.0, 7.0, 8.0, 9.0, 10.0, or 11.0 with HCl or NaOH.

Assay temperature: 25° C.

A 300 microliter protease sample (diluted in 0.01% Triton® X-100) was mixed with 1.5 ml of the assay buffer at the respective pH value, bringing the pH of the mixture to the pH of the assay buffer. The reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the protease activity at the pH in question. The assay was repeated with the assay buffer at the other pH values, and the activity measurements were plotted as relative activity against pH. The relative activities were normalized with the highest activity (pH-optimum), i.e. setting activity at pH-optimum to 1, or to 100%. The protease samples were diluted to ensure that all activity measurements fell within the linear part of the dose-response curve for the assay.

EXAMPLE 2C pH-Stability Assay

Suc-AAPF-pNA (Sigma® S-7388) was used for obtaining pH-stability profiles.

Assay buffer: 100 mM succinic acid, 100 mM HEPES, 100 mM CHES, 100 mM CABS, 1 mM $CaCl_2$, 150 mM KCl, 0.01% Triton® X-100 adjusted to pH-values 2.0, 2.5, 3.0, 3.5, 4.0, 4.5, 5.0, 6.0, 7.0, 8.0, 9.0, 10.0 or 11.0 with HCl or NaOH.

Each protease sample (in 1 mM succinic acid, 2 mM $CaCl_2$, 100 mM NaCl, pH 6.0 and with an $A_{280}$ absorption>10) was diluted in the assay buffer at each pH value tested to $A_{280}$=1.0. The diluted protease samples were incubated for 2 hours at 37° C. After incubation, protease samples were diluted in 100 mM succinic acid, 100 mM HEPES, 100 mM CHES, 100 mM CABS, 1 mM $CaCl_2$, 150 mM KCl, 0.01% Triton® X-100, pH 9.0, bringing the pH of all samples to pH 9.0.

In the following activity measurement, the temperature was 25° C.

300 microliters diluted protease sample was mixed with 1.5 ml of the pH 9.0 assay buffer and the activity reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the (residual) protease activity. The 37° C. incubation was performed at the different pH-values and the activity measurements were plotted as residual activities against pH. The residual activities were normalized with the activity of a parallel incubation (control), where the protease was diluted to $A_{280}$=1.0 in the assay buffer at pH 9.0 and incubated for 2 hours at 5° C. before activity measurement as the other incubations. The protease samples were diluted prior to the activity measurement in order to ensure that all activity measurements fell within the linear part of the dose-response curve for the assay.

EXAMPLE 2D

Temperature-Activity Assay

Protazyme AK tablets were used for obtaining temperature profiles. Protazyme AK tablets are azurine dyed crosslinked casein prepared as tablets by Megazyme.

Assay buffer: 100 mM succinic acid, 100 mM HEPES, 100 mM CHES, 100 mM CABS, 1 mM $CaCl_2$, 150 mM KCl, 0.01% Triton® X-100 adjusted to pH 9.0 with NaOH.

A Protazyme AK tablet was suspended in 2.0 ml 0.01% Triton® X-100 by gentle stirring. 500 microliters of this suspension and 500 microliters assay buffer were mixed in an Eppendorf tube and placed on ice. 20 microliters protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate. By transferring the tube back to the ice bath, the assay incubation was stopped. The tube was centrifuged in an ice-cold centrifuge for a few minutes and the $A_{650}$ of the supernatant was read by a spectrophotometer. A buffer blind was included in the assay (instead of enzyme). $A_{650}$(protease)-$A_{650}$(blind) was a measurement of protease activity. The assay was performed at different temperatures and the activity measurements were plotted as relative activities against incubation temperature. The relative activities were normalized with the highest activity (temperature optimum). The protease samples were diluted to ensure that all activity measurements fell within the near linear part of the dose-response curve for the assay.

Figure 1:
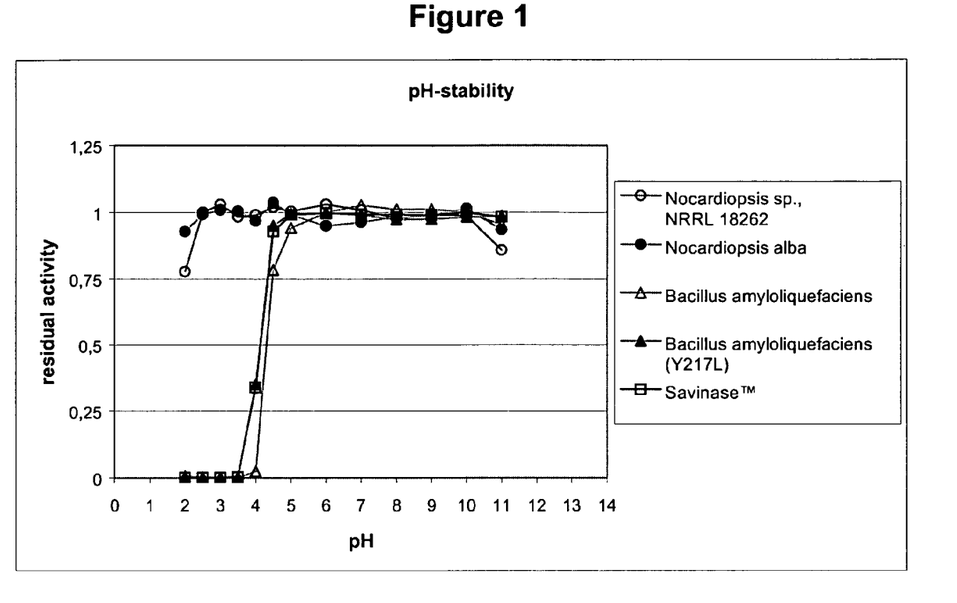
FIG. 1 shows pH-stability curves, viz. residual protease activity of five proteases (two acid-stable proteases derived from *Nocardiopsis*, and three reference proteases (Sub. Novo and Sub. Novo (Y217L), both derived from *Bacillus amyloliquefaciens*, and SAVINAS™) after incubation for 2 hours, at a temperature of 37° C., and at pH-values in the range of pH 2 to pH 11; the activity is relative to residual activity after a 2 hour incubation at pH 9.0, and 5° C.
Figure 2:
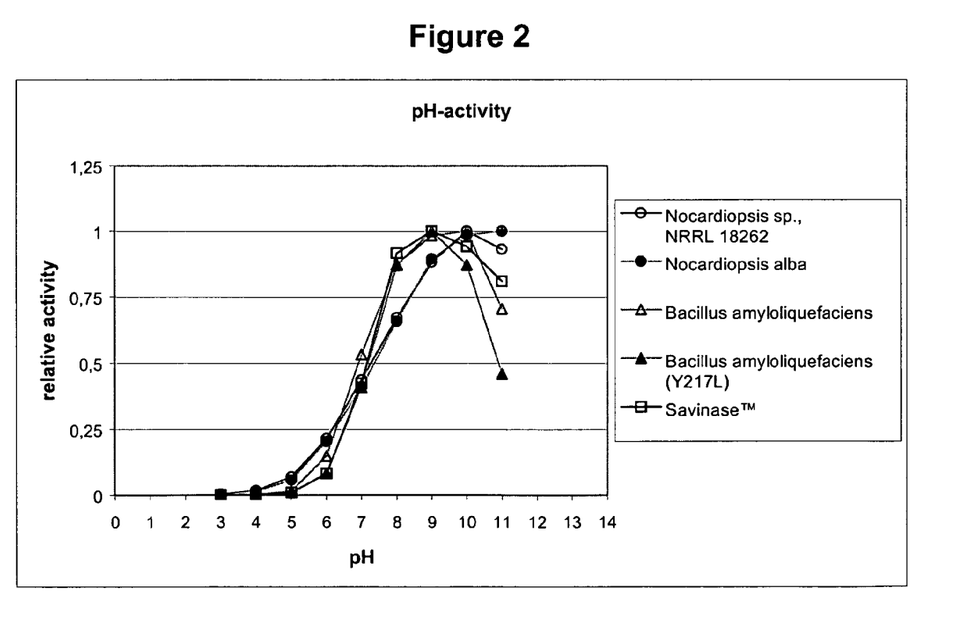
FIG. 2 shows pH-activity curves, viz. protease activity between pH 3 and pH 11, relative to the protease activity at pH-optimum, of the same five proteases.
Figure 3:
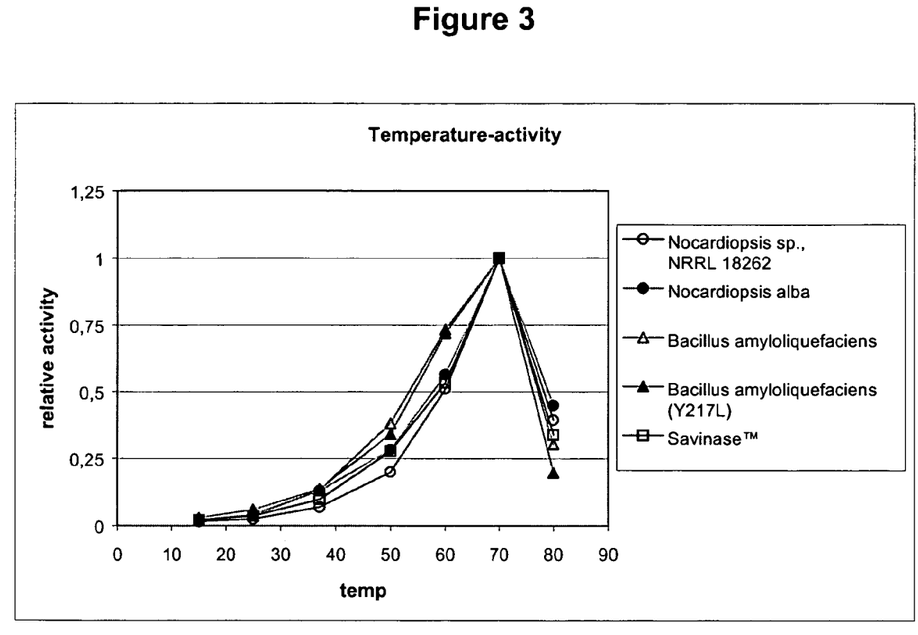
FIG. 3 shows temperature-activity curves at pH 9.0, viz. protease activity at pH 9.0 between 15° C. and 80° C., relative to protease activity at the optimum temperature, of the same five proteases.

An overview of the activity optima (pH- and temperature activity) is seen in Table 1. pH-stability, pH-activity and temperature-activity profiles are seen in FIGS. 1-3, and a detailed comparison of the pH-stability data for the proteases at acidic pH-values is seen in Table 2.

TABLE 1 pH- and temperature optima of various proteases

| Protease | pH-optimum (pNA-substrate) | Temperature-optimum at pH 9.0 (Protazyme AK) |
|---|---|---|
| Nocardiopsis sp. NRRL 18262 | 10 | 70° C. |
| Nocardiopsis alba | 11 | 70° C. |
| Sub. Novo[1] | 10 | 70° C. |
| Sub. Novo (Y217L)[2] | 9 | 70° C. |
| SAVINASE ™[3] | 9 | 70° C. |

EXAMPLE 2E

Absorption Purity of Purified Protease Samples

Determination of $A_{280}/A_{260}$ Ratio

The $A_{280}/A_{260}$ ratio of purified protease samples was determined as follows.

$A_{260}$ means the absorption of a protease sample at 260 nm in a 1 cm path length cuvette relative to a buffer blank. $A_{280}$ means the absorption of the same protease sample at 280 nm in a 1 cm path length cuvette relative to a buffer blank.

Samples of the purified proteases from Example 2 were diluted in buffer until the $A_{280}$ reading of the spectrophotometer is within the linear part of its response curve. The $A_{280}/A_{260}$ ratio was determined from the readings: For Nocardiopsis sp. NRRL 18262 1.83, and for Nocardiopsis alba 1.75.

EXAMPLE 3

Ability of Protease Derived from Nocardiopsis sp. NRRL 18262 to Degrade Insoluble Parts of Soy Bean Meal (SBM)

The protease from Nocardiopsis sp. NRRL 18262 was tested for its ability to make the insoluble/indigestible parts of SBM accessible to digestive enzymes and/or added exogeneous enzymes.

Its performance was compared to two aspartate proteases, Protease I and Protease II, prepared as described in WO 95/02044. This document also discloses their use in feed. Protease I is an Aspergillopepsin II type of protease, and Protease II an Aspergillopepsin I type of protease (both aspartate proteases, i.e. non-subtilisin proteases) from Aspergillus aculeatus (reference being made to Handbook of Proteolytic Enzymes referred to above).

The test substrate, the so-called soy remnant, was produced in a process which mimics the digestive tract of mono-gastric animals, including a pepsin treatment at pH 2, and a pancreatin treatment at pH 7.

In the pancreatin treatment step a range of commercial enzymes was added in high dosages in order to degrade the SBM components that are accessible to existing commercial enzymes.

The following enzymes, all commercially available from Novozymes A/S, Denmark, were added: ALCALAS™ 2.4L, NEUTRASE™ 0.5L, FLAVOURZYME™ 1000L, ENERGEX™ L, BIOFEED™ Plus L, PHYTASE NOVO™ L. The SBM used was a standard 48% protein SBM for feed, which had been pelletized.

After the treatment only 5% of the total protein was left in the resulting soy remnant.

TABLE 2 pH-stability of various proteases, between pH 2.0 and 5.0

| Protease | pH 2.0 | pH 2.5 | pH 3.0 | pH 3.5 | pH 4.0 | pH 4.5 | pH 5.0 |
|---|---|---|---|---|---|---|---|
| Nocardiopsis sp. NRRL 18262 | 0.779 | 1.000 | 1.029 | 0.983 | 0.991 | 1.019 | 1.004] |
| Nocardiopsis alba | 0.929 | 0.993 | 1.009 | 1.005 | 0.969 | 1.037 | 0.992 |
| Sub. Novo | 0.007 | 0.003 | 0.000 | 0.000 | 0.024 | 0.784 | 0.942 |
| Sub. Novo (Y217L) | 0.000 | 0.000 | 0.002 | 0.003 | 0.350 | 0.951 | 0.996 |
| Savinase ® | 0.001 | 0.001 | 0.001 | 0.003 | 0.338 | 0.929 | 0.992 |

FITC Labelling Protocol

The remnant was subsequently labelled with FITC (Molecular Probes, F-143) as follows: Soy remnant (25 g wet, ~5 g dry) was suspended in 100 ml 0.1 M carbonate buffer, pH 9 and stirred 1 hour at 40° C. The suspension was cooled to room temperature and treated with fluorescein 5-isothiocyanate (FITC) over night in the dark. Non-coupled probe was removed by ultrafiltration (10.000 Mw cut-off).

FITC-Assay

The FITC-labelled soy remnant was used for testing the ability of the proteases to degrade the soy remnant using the following assay: 0.4 ml protease sample (with $A_{280}$=0.1) was mixed with 0.4 ml FITC-soy remnant (suspension of 10 mg/ml in 0.2 M sodium-phosphate buffer pH 6.5) at 37° C., and the relative fluorescence units (RFU 485/535 nm; excitation/monitoring wave length) measured after 0 hours, and after 22 hours incubation. Before determination of the RFU, samples were centrifuged for 1 min at 20.000×G and 250 microliter supernatant was transferred to a black micro-titer tray. Measurements were performed using a VICTOR 1420 Multilabel counter (In vitro, Denmark). RFU is generally described by Iain D. Johnson in: Introduction to Fluorescence Techniques, Handbook of Fluorescent Probes and Research Chemicals, Molecular Probes, Richard P. Haugland, $6^{th}$ edition, 1996 (ISBN 0-9652240-0-7).

A blind sample was prepared by adding 0.4 ml buffer instead of enzyme sample. $RFU_{sample}=\Delta RFU_{sample}-\Delta RFU_{blind}$, where $\Delta RFU=RFU(22\ hours)-RFU(0\ hours)$ The resulting FITC values ($RFU_{sample}$ values) are shown in Table 3 below. The FITC values are generally with an error margin of +/−20.000. Contrary to Protease I and Protease II, the protease derived from *Nocardiopsis* sp. NRRL 18262 degraded the soy remnant to a significant extent.

TABLE 3

Ability of proteases to degrade soy remnant

| Protease | FITC (+/−20000) |
|---|---|
| *Nocardiopsis* sp. NRRL 18262 | 92900 |
| Protease I | −9200 |
| Protease II | −1200 |

EXAMPLE 4

In Vitro Testing of the Protease Derived from *Nocardiopsis* sp. NRRL 18262

The protease derived from *Nocardiopsis* sp. NRRL 18262 was tested, together with a protease derived from *Bacillus* sp. NCIMB 40484 ("PD498," prepared as described in Example 1 of WO 93/24623), and together with FLAVOURZYME™, a protease-containing enzyme preparation from *Aspergillus oryzae* (commercially available from Novozymes A/S, Bagsvaerd, Denmark), for its ability to solubilize maize-SBM (maize-Soy Bean Meal) proteins in an in vitro digestion system (simulating digestion in monogastric animals). For the blank treatments, maize-SBM was incubated in the absence of exogenous proteases.

Outline of in vitro model

| Components added to flask | Time course (min) |
|---|---|
| 10 g maize-SBM (60:40) + HCl/pepsin (3000 U/g diet) + protease (0.1 mg enzyme protein/g diet or 3.3 mg FLAVOURZYME ™/g diet), T = 40° C., pH = 3.0 | t = 0 |
| NaOH, T = 40° C., pH 6 | t = 60 |
| NaHCO₃/pancreatin (8.0 mg/g diet), T = 40° C., pH 6-7 | t = 80 |
| Stop incubation and take samples, T = 0° C. | t = 320 |

Substrates 10 g maize-SBM diet with a ratio maize-SBM of 6:4 (w/w) was used. The protein content was 43% (w/w) in SBM and 8.2% (w/w) in maize meal. The total amount of protein in 10 g maize-SBM diet was 2.21 g.

Digestive Enzymes

Pepsin (Sigma P-7000; 539 U/mg, solid), pancreatin (Sigma P-7545; 8×U.S.P. (US Pharmacopeia)).

Enzyme Protein Determinations

The amount of protease enzyme protein is calculated on the basis of the $A_{280}$ values and the amino acid sequences (amino acid compositions) using the principles outlined in S. C. Gill & P. H. von Hippel, Analytical Biochemistry 182, 319-326, (1989).

Experimental Procedure for In Vitro Model 1. 10 g of substrate is weighed into a 100 ml flask.
2. At time 0 min, 46 ml HCl (0.1 M) containing pepsin (3000 U/g diet) and 1 ml of protease (0.1 mg enzyme protein/g diet, except for FLAVOURZYME™: 3.3 mg/g diet) are added to the flask while mixing. The flask is incubated at 40° C.
3. At time 20-25 min, pH is measured.
4. At time 45 min, 16 ml of H₂O is added.
5. At time 60 min, 7 ml of NaOH (0.4 M) is added.
6. At time 80 min, 5 ml of NaHCO₃ (1 M) containing pancreatin (8.0 mg/g diet) is added.
7. At time 90 min, pH is measured.
8. At time 300 min, pH is measured.
9. At time 320 min, aliquots of 30 ml are removed and centrifuged (10000×g, 10 min, 0° C.).
10. Total soluble protein in supernatants is determined.

Protein Determination

Supernatants are analyzed for protein content using the Kjeldahl method (determination of % nitrogen; A.O.A.C. (1984) Official Methods of Analysis $14^{th}$ ed. Association of Official Analytical Chemists, Washington D.C.).

Calculations

For all samples, in vitro protein solubility was calculated using the equations below.

Amount of protein in diet sample: 22.1% of 10 g=2.21 g

If all the protein were solubilized in the 75 ml of liquid, the protein concentration in the supernatant would be: 2.21 g/75 ml≈2.95%.

Note that the supernatants also include the digestive and exogenous enzymes. In order to determine the solubility, the protein contribution from the digestive and exogenous enzymes should be subtracted from the protein concentrations in the supernatants whenever possible.

% protein from the pancreatin ($X$ mg/g diet) and pepsin ($YU$/g diet)=(($X$ mg pancreatin/g diet×10 g diet×0.69×100%)/(1000 mg/g×75 g))+(($YU$ pepsin/g diet×10 g diet×0.57×100%)/(539 U/mg× 1000 mg/g×75 g)), where 0.69 and 0.57 refer to the protein contents in the pancreatin and pepsin preparations used (i.e. 69% of the pancreatin, and 57% of the pepsin is protein as determined by the Kjeldahl method referred to above).

% protein from exogenous enzymes ($Z$ mg EP/g diet)= ($Z$ mg $EP$/g diet×10 g diet×100%)/(1000 mg/g×75 g)

% protein corrected in supernatant=% protein in supernatant as analyzed−(% protein from digestive enzymes+% protein from exogenous enzymes)

Protein solubilization (%)=(% protein corrected in supernatant×100%)/2.95%

The results below show that the protease derived from *Nocardiopsis* sp. NRRL 18262 has a significantly better effect on protein solubilization as compared to the blank, and as compared to the *Bacillus* sp. NCIMB 40484 protease.

| Enzyme | Solubilized P (% of total) | SD | n |
|---|---|---|---|
| Blind (no exogenous enzymes) | 73.8[c] | 0.87 | 10 |
| + the protease derived from *Nocardiopsis* sp. NRRL 18262 | 77.5[a] | 0.50 | 10 |
| + the protease derived from *Bacillus* sp. NCIMB 40484 | 75.6[b] | 1.52 | 5 |
| + FLAVOURZYME ™ | 74.1[c] | 0.23 | 4 |

[a,b,c]Values within a column not sharing a common superscript letter are significantly different, $P < 0.05$.
SD is standard deviation;
n is the number of observations.

EXAMPLE 5

Degradation of the Lectin SBA and the Soybean Bowman-Birk and Kunitz Inhibitors

The ability of the proteases from *Nocardiopsis* sp. NRRL 18262 and *Bacillus* sp. NCIMB 40484 to hydrolyze soybean agglutinin (SBA) and the soy Bowman-Birk and Kunitz trypsin inhibitors was tested.

Pure SBA (Fluka 61763), Bowman-Birk Inhibitor (Sigma T-9777) or Kunitz Inhibitor (Trypsin Inhibitor from soybean, Boehringer Mannheim 109886) was incubated with the protease for 2 hours, 37° C., at pH 6.5 (protease: anti-nutritional factor=1:10, based on $A_{280}$). Incubation buffer: 50 mM dimethyl glutaric acid, 150 mM NaCl, 1 mM $CaCl_2$, 0.01% Triton X-100, pH 6.5.

The ability of the proteases to degrade SBA and the protease inhibitors was estimated from the disappearance of the native SBA or trypsin inhibitor bands and appearance of low molecular weight degradation products on SDS-PAGE gels. Gels were stained with Coomassie blue and band intensity determined by scanning.

The results, as % of anti-nutritional factor degraded, are shown in Table 4 below.

It is contemplated that the ability to degrade the anti-nutritional factors in soy can also be estimated by applying the Western technique with antibodies against SBA, Bowman-Birk Inhibitor or Kunitz Inhibitor after incubation of soybean meal with the candidate proteases (see WO 98/56260).

TABLE 4

| Protease derived from | SBA | Bowman-Birk Inhibitor | Kunitz Inhibitor |
|---|---|---|---|
| *Nocardiopsis* sp. NRRL 18262 | 75 | 25 | 100 |
| *Bacillus* sp. NCIMB 40484 | 21 | 41 | 100 |

EXAMPLE 6

Effects of Acid-Stable *Nocardiopsis* Proteases on the Growth Performance of Broiler Chickens The trial is carried out in accordance with the official French instructions for experiments with live animals. Day-old broiler chickens ('Ross PM3'), separated by sex, are supplied by a commercial hatchery.

The chickens are housed in wire-floored battery cages, which are kept in an environmentally controlled room. Feed and tap water is provided ad libitum.

On day 8, the chickens are divided by weight into groups of 6 birds, which are allocated to either the control treatment, receiving the experimental diet without enzymes, or to the enzyme treatment, receiving the experimental diet supplemented with 100 mg enzyme protein of the protease per kg feed.

Each treatment is replicated with 12 groups, 6 groups of each sex. The groups are weighed on days 8 and 29. The feed consumption of the intermediate period is determined and body weight gain and feed conversion ratio are calculated.

The experimental diet is based on maize starch and soybean meal (44% crude protein) as main ingredients (Table 5). The feed is pelleted (die configuration: 3×20 mm) at about 70° C. An appropriate amount of the protease is diluted in a fixed quantity of water and sprayed onto the pelleted feed. For the control treatment, adequate amounts of water are used to handle the treatments in the same way.

For the statistical evaluation, a two factorial analysis of variance (factors: treatment and sex) is carried out, using the GLM procedure of the SAS package (SAS Institute Inc., 1985). Where significant treatments effects ($p<0.05$) are indicated, the differences between treatment means are analyzed with the Duncan test. An improved weight gain, and/or an improved feed conversion, and/or improved nutritive value of soybean meal is expected (taking into consideration that maize starch is a highly digestible ingredient).

REFERENCES

EEC (1986): Directive de la Commission du 9 avril 1986 fixant la méthode de calcul de la valeur énergetique des aliments composés destinés à la volaille. Journal Officiel des Communautés Européennes, L130, 53-54

SAS Institute Inc. (1985): SAS® User's Guide, Version 5 Edition. Cary N.C.

TABLE 5

Composition of the experimental diet

Ingredients (%):

| | |
|---|---|
| Maize starch | 45.80 |
| Soybean meal 44[1] | 44.40 |

TABLE 5-continued

Composition of the experimental diet

Ingredients (%):

| | |
|---|---|
| Tallow | 3.20 |
| Soybean oil | 1.00 |
| DL-Methionine | 0.18 |
| MCP | 0.76 |
| Salt | 0.05 |
| Binder | 1.00 |
| Vitamin and mineral premix | 3.55 |
| Avatec ® 15% CC [2] | 0.06 |

Analyzed content:

| | |
|---|---|
| Crude protein (%) | 19.3 |
| ME, N-corrected (MJ/kg) [3] | 12.2 |
| Crude fat (%) | 5.3 |

[1] analyzed content: 90.6% dry matter, 45.3% crude protein, 2.0% crude fat, 4.9% crude fiber
[2] corresponded to 90 mg lasalocid-Na/kg feed as anticoccidial
[3] calculated on the basis of analyzed nutrients content (EC-equation; EEC, 1986)

Supplier of Feed Ingredients
 Maize starch: Roquettes Frères, F-62136 Lestrem, France
 Soybean meal 44: Rekasan GmbH, D-07338 Kaulsdorf, Germany
 Tallow: Fondoirs Gachot SA, F-67100 Strasbourg, France
 Soybean oil: Ewoco Sarl, F-68970 Guemar, France
 DL-Methionine: Produit Roche SA, F-92521 Neuilly-sur-Seine, France
 MCP: Brenntag Lorraine, F-54200 Toul, France
 Salt: Minoterie Moderne, F-68560 Hirsingue, France
 Binder: Minoterie Moderne, F-68560 Hirsingue, France
 Premix (AM vol chair NS 4231): Agrobase, F-01007 Bourg-en-Bresse, France
 Avatec: Produit Roche SA, F-92521 Neuilly-sur-Seine, France

EXAMPLE 7

Premix and Diets for Turkey and Salmonids Supplemented with Acid-Stable *Nocardiopsis* Proteases.

A premix of the following composition is prepared (content per kilo):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mg | Vitamin B12 |
| 12333 | mg | Niacin |
| 33333 | mg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |

To this premix the protease from *Nocardiopsis* sp. NRRL 18262 is added (prepared as described in Example 2), in an amount corresponding to 10 g protease enzyme protein/kg.

Pelleted turkey starter and grower diets with a composition as shown in the below table (on the basis of Leeson and Summers, 1997 but recalculated without meat meal by using the AGROSOFT®, optimisation program) and with 100 mg protease enzyme protein per kg are prepared as follows:

Milled maize, Soybean meal, Fish-meal and Vegetable fat are mixed in a cascade mixer. Limestone, calcium phosphate and salt are added, together with the above premix in an amount of 10 g/kg diet, followed by mixing. The resulting mixture is pelleted (steam conditioning followed by the pelleting step).

| Ingredient | Starter diet, g/kg | Grower, g/kg | Finisher |
|---|---|---|---|
| Maize | 454.4 | 612.5 | 781.0 |
| Soybean meal | 391 | 279 | 61.7 |
| Fish meal | 70 | 29.9 | 70 |
| Vegetable fat | 21 | 21 | 46 |
| Limestone | 19 | 16.9 | 9 |
| Calcium phosphate | 30 | 25.9 | 16.8 |
| Salt (NaCl) | 2 | 2 | 2 |
| Vitamin and mineral premix | 10 | 10 | 10 |
| Lysine | 1.3 | 1.49 | |
| Methionine | 1.3 | 1.3 | 3.6 |
| Calculated nutrients | | | |
| Crude protein g/kg | 279 | 213 | 152 |
| Metabolizable energy MJ/kg | 12.3 | 12.7 | 14.1 |
| Calcium, g/kg | 15.8 | 12.7 | 9 |
| Available Phosphorus, g/kg | 8.2 | 6.4 | 4.6 |
| Lysine, g/kg | 17.6 | 12.8 | 7.5 |
| Methionine, g/kg | 6.1 | 4.9 | 6.9 |

Two diets for Salmonids are also prepared, as generally outlined above. The actual compositions are indicated in the Table below (compiled from Refstie et al (1998), Aquaculture, vol. 162, p.301-302). The estimated nutrient content is recalculated by using the Agrosoft® feed optimisation program.

The protease derived from *Nocardiopsis alba*, prepared as described in Example 2, is added to the diets in an amount corresponding to 100 mg protease enzyme protein per kg.

| Ingredient | Conventional diet with fish meal | Alternative diet with soybean meal |
|---|---|---|
| Wheat | 245.3 | 75.2 |
| Fish meal | 505.0 | 310.0 |
| Soybean meal | — | 339.0 |
| Fish oil | 185.0 | 200.0 |
| DL-Methionine | 13.9 | 23.0 |
| Mono-Calcium phosphate | — | 2.0 |
| Vitamin and Mineral premix + pellet binder and astaxanthin | 50.8 | 50.8 |
| Calculated nutrients (fresh weight basis) | | |
| Crude protein g/kg | 401 | 415 |
| Crude fat g/kg | 232 | 247 |
| Metabolizable energy MJ/kg | 16.9 | 16.5 |
| Calcium, g/kg | 13.9 | 9.8 |
| Phosphorus, g/kg | 10.8 | 9.0 |

|  | Conventional diet with fish meal | Alternative diet with soybean meal |
| --- | --- | --- |
| Lysine, g/kg | 27.7 | 26.7 |
| Methionine, g/kg | 24.4 | 31.6 |

EXAMPLE 8

Determination of Purity of Protease-Containing Enzyme Products

The purity of protease-containing enzyme products, e.g. protease preparations such as commercial multi-component enzyme products, can be determined by a method based on the fractionation of the protease-containing enzyme product on a size-exclusion column. Size-exclusion chromatography, also known as gel filtration chromatography, is based on a porous gel matrix (packed in a column) with a distribution of pore sizes comparable in size to the protein molecules to be separated. Relatively small protein molecules can diffuse into the gel from the surrounding solution, whereas larger molecules will be prevented by their size from diffusing into the gel to the same degree. As a result, protein molecules are separated according to their size with larger molecules eluting from the column before smaller ones.

Protein Concentration Assay.

The protein concentration in protease-containing enzyme products is determined with a BCA protein assay kit from PIERCE (identical to PIERCE cat. No.23225). The sodium salt of Bicinchoninic acid (BCA) is a stable, water-soluble compound capable of forming an intense purple complex with cuprous ions ($Cu^{1+}$) in an alkaline environment. The BCA reagent forms the basis of the BCA protein assay kit capable of monitoring cuprous ions produced in the reaction of protein with alkaline $Cu^{2+}$ (Biuret reaction). The color produced from this reaction is stable and increases in a proportional fashion with increasing protein concentrations (Smith, P. K., et al. (1985), Analytical Biochemistry, vol. 150, pp. 76-85). The BCA working solution is made by mixing 50 parts of reagent A with 1 part reagent B (Reagent A is PIERCE cat. No. 23223, contains BCA and tartrate in an alkaline carbonate buffer; reagent B is PIERCE cat. No. 23224, contains 4% $CuSO_4*5H_2O$). 300 microliter sample is mixed with 3.0 ml BCA working solution. After 30 minutes at 37° C., the sample is cooled to room temperature and $A_{490}$ is read as a measure of the protein concentration in the sample. Dilutions of Bovine serum albumin (PIERCE cat. No. 23209) are included in the assay as a standard.

Sample Pre-Treatment.

If the protease-containing enzyme product is a solid, the product is first dissolved/suspended in 20 volumes of 100 mM $H_3BO_3$, 10 mM 3,3'-dimethylglutaric acid, 2 mM $CaCl_2$, pH 6 (Buffer A) for at least 15 minutes at 5° C., and if the enzyme at this stage is a suspension, the suspension is filtered through a 0.45 micron filter to give a clear solution. The solution is from this point treated as a liquid protease-containing enzyme product.

If the protease-containing enzyme product is a liquid, the product is first dialyzed in a 6-8000 Da cut-off SpectraPor dialysis tube (cat.no. 132 670 from Spectrum Medical Industries) against 100 volumes of Buffer A+150 mM NaCl (Buffer B) for at least 5 hours at 5° C., to remove formulation chemicals that could give liquid protease-containing enzyme products a high viscosity, which is detrimental to the size-exclusion chromatography.

The dialyzed protease-containing enzyme product is filtered through a 0.45 micron filter if a precipitate was formed during the dialysis. The protein concentration in the dialyzed enzyme product is determined with the above described protein concentration assay and the enzyme product is diluted with Buffer B, to give a sample ready for size-exclusion chromatography with a protein concentration of 5 mg/ml. If the enzyme product has a lower than 5 mg/ml protein concentration after dialysis, it is used as is.

Size-Exclusion Chromatography.

A 300 ml HiLoad26/60 Superdex75 pg column (Amersham Pharmacia Biotech) is equilibrated in Buffer B (Flow: 1 ml/min). 1.0 ml of the protease-containing enzyme sample is applied to the column and the column is eluted with Buffer B (Flow: 1 ml/min). 2.0 ml fractions are collected from the outlet of the column, until all of the applied sample has eluted from the column. The collected fractions are analyzed for protein content (see above Protein concentration assay) and for protease activity by appropriate assays. An example of an appropriate assay is the Suc-AAPF-pNA assay (see Example 2B). Other appropriate assays are e.g. the CPU assay (se Example 1), and the Protazyme AK assay (see Example 2D). The conditions, e.g. pH, for the protease activity assays are adjusted to measure as many proteases in the fractionated sample as possible. The conditions of the assays referred to above are examples of suitable conditions. Other suitable conditions are mentioned above in the section dealing with measurement of protease activity. A protein peak with activity in one or more of the protease assays is defined as a protease peak. The purity of a protease peak is calculated as the protein amount in the peak divided with the total protein amount in all identified protease peaks.

The purity of a protease-containing enzyme product is calculated as the amount of protein in the acid-stable protease peak divided with the protein amount in all identified protease peaks using the above procedure.

We claim:

1. A method for improving the nutritional value of an animal feed, comprising adding to the animal feed an acid-stable protease that comprises an amino acid sequence having an identity of at least 90% to SEQ ID NO: 1.

2. The method of claim 1, wherein the protease comprises an amino acid sequence having an identity of at least 95% to SEQ ID NO: 1.

3. The method of claim 1, wherein the protease has a pH optimum of 8-11 and a temperature optimum of at least 70° C.

4. The method of claim 1, wherein the dosage of the protease is 0.01-200 mg protease enzyme protein per kg animal feed.

5. A method for improving the nutritional value of a vegetable protein mixture, comprising adding an acid-stable protease to the vegetable protein mixture, wherein the protease comprises an amino acid sequence having an identity of at least 90% to SEQ ID NO: 1.

6. The method of claim 5, wherein the protease comprises an amino acid sequence having an identity of at least 95% to SEQ ID NO: 1.

7. The method of claim 5, wherein the protease has a pH optimum of 8-11 and a temperature optimum of at least 70° C.

8. The method of claim 5, wherein the vegetable protein mixture comprises soybean.

* * * * *

UNITED STATES PATENT AND TRADEMARK OFFICE
CERTIFICATE OF CORRECTION

PATENT NO. : 7,658,965 B2  Page 1 of 1
APPLICATION NO. : 10/713394
DATED : February 9, 2010
INVENTOR(S) : Sjøholm et al.

It is certified that error appears in the above-identified patent and that said Letters Patent is hereby corrected as shown below:

Title Page, Item (56) Foreign Patent Documents, delete "DE 200432" and insert -- DD 200432 -- delete "DE 2004328" and insert -- DD 2004328 --.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,658,965 B2  Page 1 of 1
APPLICATION NO. : 10/713394
DATED : February 9, 2010
INVENTOR(S) : Sjoeholm et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1264 days.

Signed and Sealed this

Thirtieth Day of November, 2010

David J. Kappos
*Director of the United States Patent and Trademark Office*